US00PP10344P

United States Patent [19]

Jessel, Jr.

[11] Patent Number: Plant 10,344

[45] Date of Patent: Apr. 21, 1998

[54] CARNATION PLANT NAMED 'CFPC HALO'

[75] Inventor: Walter H. Jessel, Jr., Gonzales, Calif.

[73] Assignee: California Florida Plant Co., L.P., Salinas, Calif.

[21] Appl. No.: 711,034

[22] Filed: Sep. 10, 1996

[51] Int. Cl.[6] ..... A01H 5/00

[52] U.S. Cl. ..... Plt./70.2

[58] Field of Search ..... Plt./70.2

[56] References Cited

U.S. PATENT DOCUMENTS

P.P. 7,514 5/1991 Jessel, Jr. ..... Plt./70.6

*Primary Examiner*—Howard J. Locker

*Attorney, Agent, or Firm*—Christie, Parker & Hale, LLP

[57] ABSTRACT

A new variety of carnation plant producing white picotee red flowers.

1 Drawing Sheet

SUMMARY OF THE INVENTION

The present invention relates to a new and distinct variety of carnation plant which is the result of a cross of the variety 'Koreno' as seed parent and 'CFPC Twilight' (U.S. Plant Pat. No. 7,514) as pollen parent. The varietal denomination of this new carnation is 'CFPC Halo'.

Among the novel combination of characteristics possessed by the new variety which distinguishes it are superior resistance to *F. oxysporum*, and *F. graminearum* and white picotee red flowers. Among the differences of the new variety from its parents are flower coloration since 'CFPC Halo' produces white picotee red flowers whereas 'Koreno' flowers are yellow and 'CFPC Twilight' produces purple flowers.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary depending upon varying environmental, seasonal and cultural conditions.

The information provided herein is based on observations of plants grown inside commercial greenhouses at Salinas, Calif. The height of the plant and flower and foliage size are established as an average using standard commercial cultural practices. Where terms such as average, normal, ordinary, etc., are used, the characteristics so described are not considered distinguishing.

Name: 'CFPC Halo'

Classification:

*Botanical.*—*Dianthus caryophyllus.*

*Commercial.*—Carnation, spray type.

Parentage:

*Female seed parent.*—'Koreno'.

*Male pollen parent.*—'CFPC Twilight'.

1. Plant:
   - *Height.*—About 43 inches (first flowering).
   - *Growing habit.*—Herbaceous, semi-upright.
   - *Blooming habit.*—As a spray.
   - *Blooming season.*—Year round.
   - *Rooting time.*—About 20 days.
   - *Mutation prone.*—No.
   - *Disease resistance.*—Very good.
   - *Temperature tolerance.*—Wide range.
   - *Breaking action.*—Very good, approximately 8 to 9 lateral shoots per plant.
2. Foliage:
   - *Color.*—Upper side: Near 138A. Lower side: Near 138B.
   - *Size.*—About 7 inches long, about ¼ inches wide.
   - *Quantity.*—Numerous.
   - *Shape.*—Lanceolate.
   - *Texture.*—Smooth.
   - *Ribs.*—Central, Keeled.
   - *Arrangement.*—Bi-lateral along stem.
   - *Stem color.*—Near 137A.
3. Bud:
   - *Shape.*—Ovoid.
   - *Color.*—Near 138B.
   - *Length.*—About 1 inch.
   - *Diameter.*—About ½ inch.
4. Calyx:
   - *Number of sepals.*—About 5.
   - *Length.*—About ⅝ inch.
   - *Width.*—About ⅜ inch.
   - *Color.*—Outside — Near 138B. Inside — Near 146D.
5. Bloom:
   - *Shape.*—Round.
   - *Size.*—Diameter average: About 2¼ inches. Depth average: About 1¾ inches.
   - *Borne.*—As a spray, about 8 to 9 open flowers and buds per spray, stem length approximately 43 inches.
   - *Color.*—General tonality: White picotee red. Upper side: Whiter than 155D, red edges, near 45B. Lower side: Whiter than 155D, red edges, near 45B. Center: Whiter than 155D, red edges, near 45B. Outer petals: White with near 45B edges.
   - *Keeping quality.*—Very good, petals dry up after about 3 weeks on stem but remain attached.
   - *Fragrance.*—Slight.

6. Petals:
   *Number.*—About 35.
   *Outer petals.*—Length: About 1¼ inches. Width: About 1 inch.
   *Central petals.*—Length: About 1⅛ inches. Width: About ⅜ inch.
   *Texture.*—Smooth.
   *Form.*—Fan shaped.
   *Appearance.*—Shiny, smooth petal edge.
7. Reproductive organs:
   *Stamens.*—None (sterile).
   *Pistil.*—Number: 1 to 2. Color: White. Length: About 1 inch.
   *Stigma.*—Number: About 2. Color: White.
   *Ovary.*—Shape: Conical.
   *Color: Base — near* 158D. Body — near 146D. Apex — near 161D.
   *Fertility.*—Female: Good. Male: Sterile.

I claim:

1. A new and distinct variety of carnation plant substantially as shown and described.

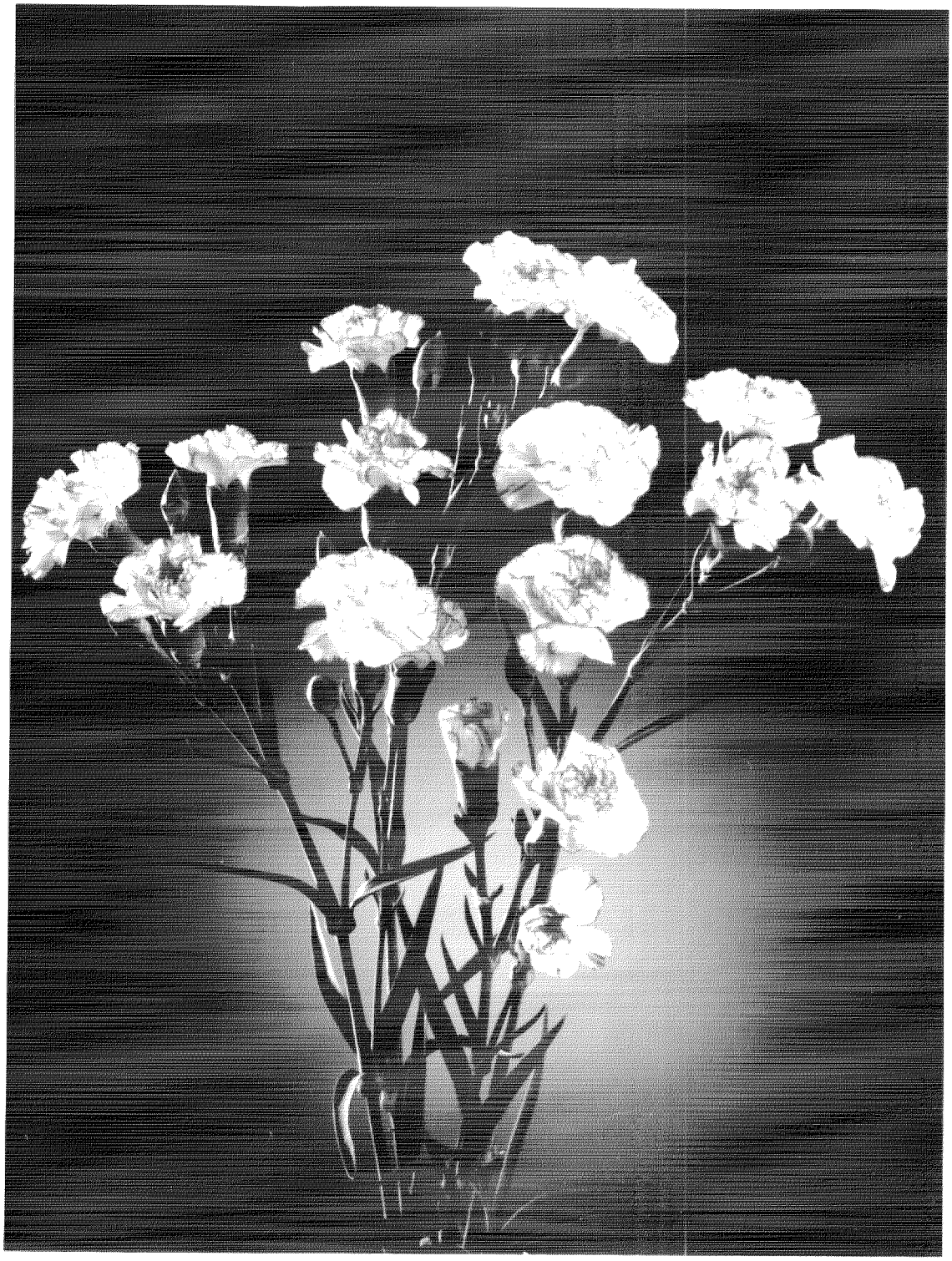

* * * * *